(12) United States Patent
Shwartz

(10) Patent No.: US 9,750,666 B2
(45) Date of Patent: Sep. 5, 2017

(54) WET WIPE

(71) Applicant: Tzvi Tuvya Shwartz, Hatzor Haglillit (IL)

(72) Inventor: Tzvi Tuvya Shwartz, Hatzor Haglillit (IL)

(*) Notice: Subject to any disclaimer, the term of this patent is extended or adjusted under 35 U.S.C. 154(b) by 145 days.

(21) Appl. No.: 14/535,116

(22) Filed: Nov. 6, 2014

(65) Prior Publication Data

US 2016/0128523 A1    May 12, 2016

(51) Int. Cl.
*B08B 1/00* (2006.01)
*A61K 8/02* (2006.01)
*A61Q 19/10* (2006.01)
*A47K 10/42* (2006.01)
*A47K 10/32* (2006.01)

(52) U.S. Cl.
CPC ............ *A61K 8/0208* (2013.01); *A61Q 19/10* (2013.01); *A47K 10/421* (2013.01); *A47K 2010/3266* (2013.01)

(58) Field of Classification Search
CPC ...................... A47K 2010/3266; A47K 10/421
USPC ................... 15/104.93, 118, 209.1
See application file for complete search history.

(56) References Cited

U.S. PATENT DOCUMENTS

| 6,716,498 | B2 | 4/2004 | Curro et al. | |
|---|---|---|---|---|
| 2005/0026802 | A1* | 2/2005 | Kilkenny | C11D 3/044 510/295 |
| 2013/0097792 | A1* | 4/2013 | DeFrancesco | A47L 13/16 15/104.94 |

FOREIGN PATENT DOCUMENTS

| EP | 1998659 A2 | 12/2008 |
|---|---|---|
| WO | 9946119 A1 | 9/1999 |
| WO | 02007701 A3 | 9/2002 |
| WO | 2010113683 A1 | 10/2010 |

* cited by examiner

*Primary Examiner* — Jennifer C Chiang
(74) *Attorney, Agent, or Firm* — PatShegen IP

(57) ABSTRACT

A wet wipe is provided including at least a first flexible layer and a second flexible layer made of a nonabsorbent material and having a liquid entrapped therebetween, wherein at least one of the first and second flexible layers is provided with a plurality of pores configured to allow the liquid to pass therethrough.

16 Claims, 2 Drawing Sheets

WET WIPE

TECHNOLOGICAL FIELD

The presently disclosed subject matter relates to a wet wipe in general, and in particular to a wet wipe comprising liquid.

BACKGROUND ART

References considered to be relevant as background to the presently disclosed subject matter are listed below:
WO9946119
EP1998659
WO0207701
U.S. Pat. No. 6,716,498
WO2010113683

Acknowledgement of the above references herein is not to be inferred as meaning that these are in any way relevant to the patentability of the presently disclosed subject matter.

BACKGROUND

The fourth commandment states "remember the Sabbath Day, to keep it holy. Six days you shall labor and do all your work; but the seventh day is a Sabbath unto the Lord your G-d. On it you shall not do any manner of work"

Accordingly, from sundown on Friday until the sun sets on Saturday, many observant Jews refrain from certain activities, which are divided to 39 major categories of labor, one of which is the act of Threshing/Extraction. Threshing or extraction, which is known in Talmudic terms as DASH, is defined as removal of an undesirable inner from a desirable outer. Extraction thus, refers to any productive extraction and includes juicing of fruits and vegetables and wringing (desirable fluids) out of cloths. As such, squeezing or wringing liquids absorbed in a fabric is as forbidden act on the Saturday. Accordingly, since the use of wet wipes, such as baby wipes, made of fabric material may be involved with a forbidden act, many observant Jews refrain from the use of wipes during the course of the Sabbath.

There are known in the art wet wipes which are made of various fabric materials. For example, WO9946119 discloses a nonwoven composite combines a support layer with at least one carded fiber layer, and the combined layers are thermally bonded together between calendar rolls. The support layer consists of a pre-bonded thermal-bond nonwoven, which provides a softer, more durable hand. The carded fiber layers can be comprised of a blend of absorbent, resilient and soft fibers. In addition, the carded fiber layer can be bonded with a different bond pattern than that of the pre-bonded thermal-bond support layer, to produce a dual textured product EP1998659 discloses Stacks of pre-moistened wipes wherein the wipes comprise a composite of at least two layers of fibrous nonwoven webs, which in turn comprise fibers with an average fiber denier from about 2.5 to about 6.0. The stacks of pre-moistened wipes are from about 50 to about 300 millimeters in height and have a saturation gradient index from about 1.0 to about 1.5.

WO0207701 discloses wet topical wipes for application to the skin, and methods of using the wipes on rough areas of the skin such as male facial skin or shaven areas of the skin, wherein the topical wipes comprise (a) a fluid entangled, nonwoven, flexible substrate having a Substrate Residue Value of from about 0.1 mg/cm2 to about 1.2 mg/cm2, and (b) an aqueous carrier contained within the flexible substrate.

U.S. Pat. No. 6,716,498 discloses a substance encapsulation system capable of being apertured under a tensioning force comprises a first web and a second web. A powdered, granular, particulate, or gel substance can be disposed between the first and second webs. Upon application of a sufficient force having a vector component parallel to the transverse axis, the bond site fractures to form a corresponding aperture to facilitate exposure of the substance. Alternatively, a central layer may be disposed between at least a portion of the first and second webs. The central layer may carry a substance to be exposed or the central layer may be a dissimilar material from the first and second webs.

WO2010113683 discloses a sheet-like cosmetic comprising a liquid composition and a non-woven fabric impregnated with the liquid composition: wherein the nonwoven fabric comprises hydrophilic fibers and hydrophobic fibers, in which the ratio of the amount of the hydrophilic fibers to the amount of the hydrophobic fibers [i.e., a (hydrophilic fibers)/(hydrophobic fibers) ratio] is 90/10 to 50/50 by mass and wherein the liquid composition comprises (A) an N-palm oil fatty acid acyl L-arginine ethylDL pyrrolidone carboxylate, (B) a paraoxybenzoic acid ester, and (C) a polyhydric alcohol, in which the ratio of the amount of the component (A) to the amount of the component (B) [i.e., an (A)/(B) ratio] is 0.60 to 5.00 by mass and the total content of the component (A) and the component (B) is 0.15 to 0.40% by mass.

The use of fabric material even if made of a nonwoven fabric material does not overcome the problem of wringing liquids therefrom as the liquid is absorbed in the surface, and entrapped between the fibers.

General Description

An objective of the presently discloses subject matter is to provide a wet wipe which can be used without performing the act of extraction thereof.

There is provided in accordance with an aspect of the presently discloses subject matter a wet wipe including at least a first flexible layer and a second flexible layer made of a nonabsorbent material and having a liquid entrapped therebetween, wherein at least one of the first and second flexible layers is provided with a plurality of pores configured to allow the liquid to pass therethrough.

The nonabsorbent material can be an impervious material.

The first flexible layer and second flexible layer can be bonded to one another in a plurality of locations. The first flexible layer and a second flexible layer can be bonded to one another at the perimeter thereof. The first flexible layer and a second flexible layer can be configured to form together a case having a volume therebetween, the case is sealed at the perimeter thereof.

The case includes a plurality of compartment configured such that liquid from one compartment does not flow to an adjacent compartment.

The liquid can include cleaning material and/or can include moisturizing lotion.

The liquid can be configured to freely flow inside the case.

The first and second layers can be configured to allow extraction of the liquid entrapped therebetween without wringing of the wet wipe.

There is provided in accordance with another aspect of the presently disclosed subject matter a package of wet wipes including a stack of wet wipes each of which including at least one flexible layer made of a nonabsorbent impervious material and having a liquid entrapped thereby, and a body for holding said stack of wipes. The body includes a base portion configured to sealingly hold therein the stack of wet wipe and a cover portion configured to cover the base portion, and an opening for pulling a wet wipe from the stack of wet wipes out of the body. At least one of the wet wipes is disposed adjacent said opening and is readily accessible to be pulled out of said body.

The cover portion can include a side portion configured to cover the opening.

The at least a one flexible layer can include a first flexible layer and a second flexible layer made of a nonabsorbent material and having a liquid entrapped therebetween, wherein at least one of the first and second flexible layers can be provided with a plurality of pores configured to allow the liquid to pass therethrough.

The nonabsorbent material can be an impervious material.

The first flexible layer and second flexible layer can be bonded to one another in a plurality of locations. The first flexible layer and a second flexible layer can be bonded to one another at the perimeter thereof. The first flexible layer and a second flexible layer can form together a case therebetween sealed at the perimeter thereof.

The case can include a plurality of compartment configured such that liquid from one compartment does not flow to an adjacent compartment.

According to yet another example of the presently discloses subject matter there is provided a wet wipe comprising at least one flexible layer made of a nonabsorbent impervious material having an interface pattern defined thereon and liquid droplets entrapped by the interface pattern.

The interface pattern can include a plurality of ridges. The plurality of ridges can be closely disposed with respect to one another such that said liquid droplets are held therebetween.

The interface pattern can include a plurality of depressions or pores configured to hold therein liquid droplets.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1:
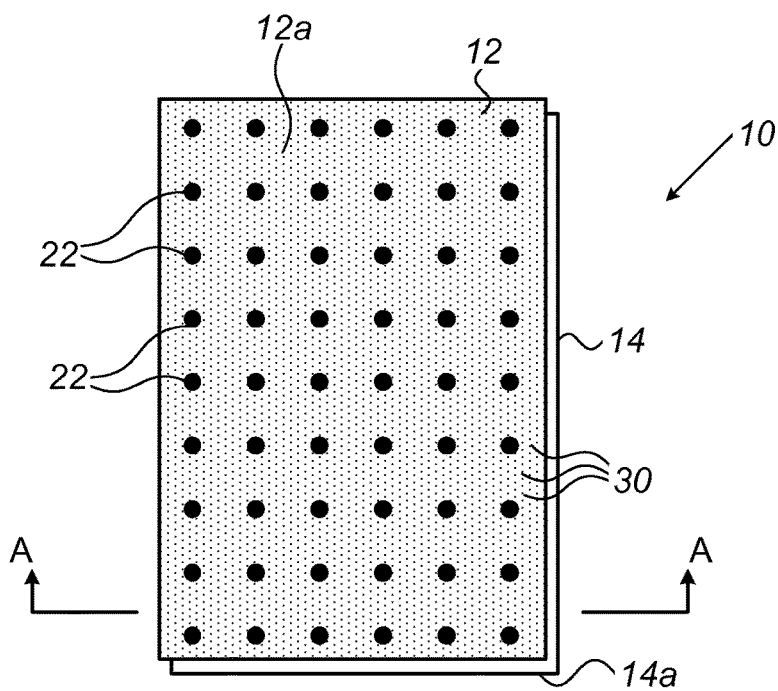
FIG. 1 is an exploded view of a wet wipe in accordance with an example of the presently disclosed subject matter.
Figure 2:
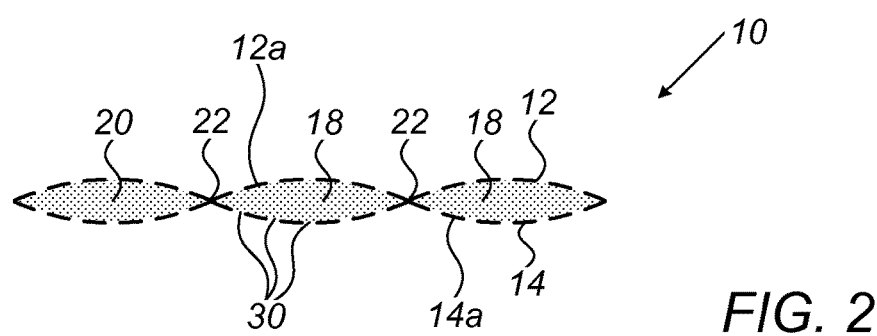
FIG. 2 is a side view of a portion of the wet wipe of FIG. 1, taken along line A-A.

FIGS. 1 and 2 shows a wet wipe 10 having a first flexible layer 12 and a second flexible layer 14 made of a nonabsorbent material and having a plurality of pores 30 configured to allow liquid to pass therethrough. The first and second flexible layers 12, 14 can be made of nylon, linear low-density polyethylene (LLDPE), PE-LD or any other polyamide materials, such as Polytetrafluoroethylene (PTFE) etc, which allow wiping therewith, however which is substantially impermeable to liquids, such that no liquid is absorbed therein.

The first and second flexible layers 12, 14 are coupled to one another such that liquid 20 can be disposed therein. The liquid 20 can be any desired cleaning liquid configured to facilitate the cleaning of surfaces such as countertops, or cleaning material for skin cleaning, such as for facial cleaning or liquid used with baby wipes, etc.

The first and second flexible layers 12, 14 can be coupled to one another at various locations forming thereby therebetween an inner volume in which the liquid 20 can be maintained.

According to an example of the presently disclosed subject matter the first and second flexible layers 12 and 14 are coupled to one another by welding a portion of the surfaces thereof such that the two surfaces are bonded together. For example, the first and second flexible layers 12 and 14 can be welded at the perimeter thereof, thereby forming a case 18 having an inner volume configured to hold liquid. Bonding of the first and second flexible layers 12 and 14 can be carried out in any known method, including but not limited to adhesive bonding, welding, sewing, etc.

It will be appreciated by those skilled in the art that the amount of liquid held between the first and second flexible layers 12 and 14 can vary in accordance with the intended use of the wet wipe 10, thus the size of the inner volume and the shape and dimension of the case 18 can be determined accordingly.

According to the illustrated example the first and second flexible layers 12 and 14 are coupled to one another about the perimeter there as well as at a plurality of bonding points 22 scattered on the surface of the first and second flexible layers 12 and 14. This way, the bonding points 22 provide additional strength and durability to the wet wipe 10. In addition, the bonding points 22 facilitate forming a substantially humongous surface without folds and wrinkles According to an example the bonding points 22 can be elongated bonding strips (not shown) defined along the length and/or the width of the first and second flexible layers 12 and 14. The elongated bonding strips can be defined such that the case 18 is divided to a plurality of compartments each of which being configured to hold a portion of the liquid 20. The compartments can be configured to independently hold the liquid with respect to other compartments, such that liquid from one compartment does not flow to an adjacent compartment. This way, the liquid contained in a specific compartment can be extracted only from pores defined on respective portion of the first and second flexible layers 12 and 14. Thus, when the wet wipe 10 is used the liquid 20 is evenly distributed on the outer surfaces 12a and 14a.

At least one of the first and second flexible layers 12 and 14 include a plurality of pores 30 configured to allow the liquid 20 to pass therethrough from the inner volume of the case 18 to the outer surface 12a of the first layers 12 and the outer surface 14a of the second layers 14, respectively.

It is appreciated that the size and shape of the pores 30 can vary in accordance with the amount of liquid inside the case 18 and the amount of liquid 20 required on the outer surfaces 12a and 14a. That is to say, the size and shape of the pores 30 can be determined in accordance with the speed in which it is desired to bring the liquid 20 to the outer surfaces 12a and 14a. For example, in a case of a baby wipe, it is desired that the liquid 20 is retained inside the case 18 until the wipe 10 engages the skin of the baby, at which point it is desired to have a sufficient amount of liquid on the outer surfaces 12a and 14a.

According to an example the pores 30 can be configured such that all the liquid 20 passes therethrough rapidly, thereby providing the outer surfaces 12a and 14a with substantially all the liquid 20 from the case 18. According to another example, the pores can be configured such that in normal conditions, such as when the wipe 10 is not in use, liquid 20 inside the case 18 is maintained therein and does not flow out of the pores 30. According to this example liquid can flow out of the pores 30 only when pressure is applied on the wipe 10, for example by pressing one of the outer surfaces 12a and 14a on the skin of the baby. This can be achieved for example by forming pores 30 in which the surface tension of the liquid 20 is sufficient to hold the liquid. The pores 30 can be further configured that only a predetermined pressure applied on the outer surface 12a and 14a can overcome the surface tension allowing thereby the liquid to flow out of the case 18.

It is appreciated that the size and shape of the pores 30 can further depend on the properties of the liquid inside the case 18. That is to say, in case the liquid is oil, or include oil component, or in case the liquid has a high viscosity, the pores 30 can be made larger so as to facilitate the extraction thereof out of the case 18.

In addition, the amount of pores and the density thereof as well as the locations thereof can be determined in accordance with the amount of liquid it is desired to have on the outer surfaces 12a and 14a. Accordingly, the first and second flexible layers 12 and 14 can include substantially many pores with high density over the outer surfaces 12a and 14a, so as to allow that liquid 20 to rapidly moist the entire outer surfaces.

According to one example, the wet wipe 10 can include first flexible layers 12 having pores 30, and a second flexible layer 14 which does not include pores and can be substantially sealed and such that no liquid can flow therethrough. This way, the first flexible layers 12 can define an engaging side for engaging the surface to be moistened, while the second flexible layer 14 defines a gripping side for gripping the wet wipe 10.

It is appreciated that the first and second layers 12 and 14 are made of a flexible material such which allows wiping and cleaning of surfaces, such as countertops, facial skin, hands, etc.

On the other hand, in order to avoid the act of wringing, upon use of the wet wipe, the first and second layers 12 and 14 are made of a nonabsorbent material which is substantially impermeable to liquids. It is further noted, that in order to preclude the act of wringing of the first and second layers 12 and 14 the latter can be made of a waterproof fabrics which are resistant to penetration by liquids.

The first and second layers 12 and 14 can thus be laminated or coated with a waterproofing material such as rubber, polyvinyl chloride (PVC), polyurethane (PU), silicone elastomer, fluoropolymers, and wax.

It is appreciated that although first and second layers 12 and 14 can be made of a waterproof material, the material thereof can be breathable such which resists liquid water passing through, but allows water vapor to pass through. It is further appreciated that if the first and second layers 12 and 14 allow vapor to pass therethrough, the amount of vapor therein is such which cannot however be wringed. This way, the use of the wet wipes is not involved in any type of wringing which is forbidden on the Sabbath as explained in the above background section.

According to an example, the production of the wet wipe 10 can be carried out by coupling the first and second layers 12 and 14 to one another, and by immersion thereof in liquid, such as cleaning liquid, or by spraying liquid thereon. The liquid enters the case 18 defined therebetween through the pores 30.

Figure 3:
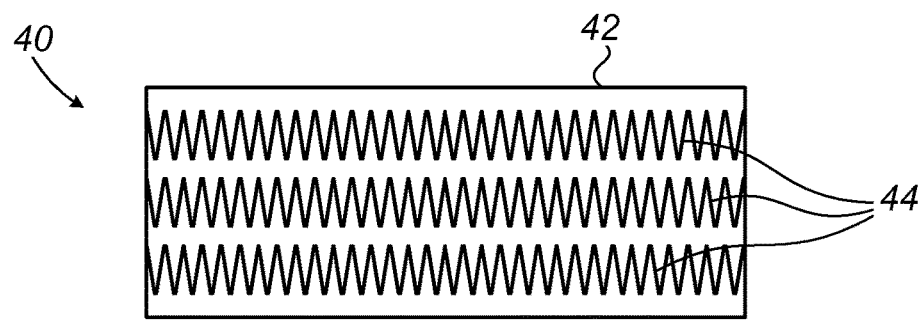
FIG. 3 is top view of a wet wipe in accordance with another example of the presently disclosed subject matter; and, FIG. 4 is a sectional view of package containing a plurality of wet wipes in accordance with an example of the presently disclosed subject matter.

Reference is now made to FIG. 3, according to a further example a wet wipe 40 can include a single layer 42 having an interface pattern defined thereon, here illustrated as a plurality of ridges 44 defined on the outer surface thereof. The ridges 44 can include a pattern configured to entrap liquid droplets between elements thereof. For example, the pattern can be a plurality of zigzag ridges closely disposed with respect to one another such that droplets are held therebetween. The liquid droplets can be held for example by the forces exerted by the surface tension of the liquid.

In addition, or alternatively, the interface pattern defined on the single layer 42 can include other elements such as a plurality of grooves, depressions, pores or apertures configured to hold therein liquid droplets, which can be held by the for example by the forces exerted by the surface tension of the liquid.

The ridges, grooves, depressions or apertures can be defined on one surface of the single layer 42 or on two surfaces thereof. In addition, the wet wipe can be a combination of a pair of flexible layers entrapping liquid therebetween, as well as ridges, grooves, depressions or apertures configured to hold liquid droplets therebetween.

The wet wipes of the present invention can be packed in a package, such which holds the liquids therein, for example a sealed package. It is appreciated that since in accordance with the present invention the liquid is not absorbed in the layers, rather it is held in the volume defined therebetween, evaporation thereof may occur at a higher rate in comparison with wet wipes having liquid absorbed in a surface thereof. Thus, the package of the wet wipes can be a sealable packages, and it can further be configured to be resealed even following an initial opening thereof.

According to an example, the production of the wet wipe 40 can be carried out by passing the single layer 42 through a volume containing steam, or vapor of any liquid, such as cleaning liquid, or by spraying liquid thereon. The liquid droplets are entrapped between the ridges, grooves, depressions or apertures defined on the outer surface thereof.

According to a further example, the single layer 42 can include solid cleaning or moisturizing material disposed thereon, for example, a powered material, cream, or particles of soap. Upon use of the wipe, the water or any other liquid is sprayed on the surface turning the wipe into a wet wipe.

Figure 4:
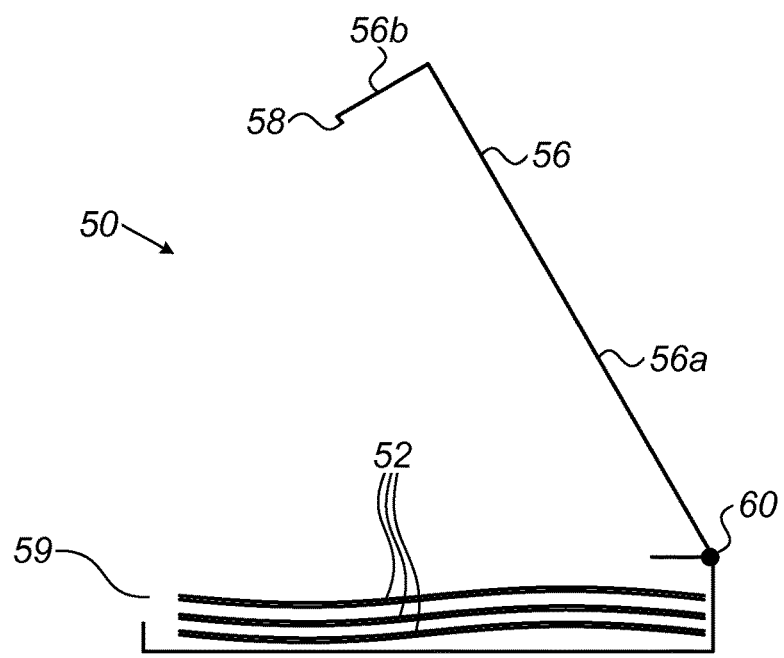

Reference is now made to FIG. 4, a package 50 for holding wet wipes 52 can include a base portion 55 configured to hold a stack of wet wipe 52 and can be configured to preclude leaking of liquid. The package 50 according to this example can include a cover 56 configured to sealingly cover the base portion 55, such that when in closed position, evaporation of the liquid held by the wet wipes 52 is precluded or at least reduced.

The wet wipes 52 can be configured to pop up one after the other, for example by folding the wet wipes to interleave with one another. It is appreciated that in some cases the wipes cannot be configured as pop up wipes, for example if the two layers with the liquid therebetween include a thickness which does not allow folding the wipes to interleave with one another. In this case, it is desired to facilitate access to the bottom of the packages, such that wet wipes at the bottom of the stack can be easily reached and pulled out.

Accordingly, the package can include a body for holding a stack of wipes and having a base portion configured to sealingly hold therein the stack of wet wipe, and a cover portion configured to cover said base portion. The body can include an opening for pulling at least one wet wipe from the stack of wet wipes out of said body;

The body can be configured such that at least one of the wet wipes is disposed adjacent the opening and is readily accessible to be pulled out of the body.

According to an example, the base portion 55 can include an opening such as a depression 59 in one of the side walls thereof such that the user hands or fingers can be inserted therethrough. In this case, the cover 56 can include a top portion 56a for covering the top of the package 50 and a side portion 56b configured to cover the depression 59. It is appreciated that the depression 59 can be replaced with a groove or any other opening allowing pulling the wet wipe out of the package 50.

According to an example the package 50 can include a sealing member 58 for sealing engagement between the cover 56 and the base portion 55, the sealing member 58 can be disposed for example at the edge of side portion 56b and can be configured to engage the side wall of the base portion 55.

The cover can be configured to pivot with respect to the base portion 55 about a hinge 60 mounted on one edge thereof.

It will be appreciated that the package 50 can be made of a rigid material or a flexible material. Further, since as explained herein above, extraction of liquid entrapped between the first and second layers or between ridges or inside grooves defined on the outer surface thereof requires applying pressure on the wet wipe, it might be desired to avoid undesired pressure applied on the stack of wet wipes disposed inside the package. Accordingly, the package, if not made of a rigid material, can for example include a reinforcing structure, such at rigid rods disposed at the corners thereof, or rigid elements disposed along the side wall thereof.

According to another example, the package can include an aperture at the top portion thereof however can be configured to have a varying volume, such that as the stack of wet wipes gets smaller the bottom wet wipes are brought closer to the top portion. This can be carried out, by providing a package with a spring mechanism at the bottom surface thereof, such that the stack of wipes is always urged upwardly. Alternatively, the package can include a string configured to be pulled thereby urging the top portion towards the wet wipe at the top of the stack.

It is appreciated that despite the above description, a regular wet wipe package can be used as well.

Those skilled in the art to which the presently disclosed subject matter pertains will readily appreciate that numerous changes, variations, and modifications can be made without departing from the scope of the invention, mutatis mutandis.

The invention claimed is:

1. A wet wipe comprising at least one flexible layer made of a nonabsorbent impervious material having a pattern defined on the outer surface thereof and liquid droplets entrapped by said pattern.

2. The wet wipe of claim 1 wherein said pattern include a plurality of ridges.

3. The wet wipe of claim 2 wherein said plurality of ridges are closely disposed with respect to one another such that said liquid droplets are held therebetween.

4. The wet wipe of claim 1 wherein said pattern include a plurality of depressions configured to hold therein liquid droplets.

5. The wet wipe of claim 1 wherein said pattern include a plurality of pores configured to hold therein liquid droplets.

6. The wet wipe of claim 5 further comprising a second flexible layer made of a nonabsorbent material and having a liquid entrapped between said first flexible layer and said second flexible layer, wherein at least one of said first and second flexible layers is provided with a plurality of pores configured to allow said liquid to pass therethrough.

7. The wet wipe of claim 6 wherein said nonabsorbent material is an impervious material.

8. The wet wipe of claim 6 wherein said first flexible layer and second flexible layer are bonded to one another in a plurality of locations.

9. The wet wipe of claim 6 wherein said first flexible layer and a second flexible layer are bonded to one another at the perimeter thereof.

10. The wet wipe of claim 9 wherein said first flexible layer and a second flexible layer form together a case having a volume therebetween, said case being sealed at the perimeter thereof.

11. The wet wipe of claim 10 wherein said case includes a plurality of compartment configured such that liquid from one compartment does not flow to an adjacent compartment.

12. The wet wipe of claim 1 wherein said liquid includes cleaning material.

13. The wet wipe of claim 1 wherein said liquid includes moisturizing lotion.

14. The wet wipe of claim 9 wherein said liquid freely flows inside said case.

15. The wet wipe of claim 1 wherein said first and second layers are configured to allow extraction of said liquid entrapped therebetween without wringing of the wet wipe.

16. The wet wipe of claim 1 wherein said pattern includes elements configured to entrap liquid droplets by forces exerted by the surface tension of the liquid.

* * * * *